(12) United States Patent
Junquera

(10) Patent No.: US 12,186,081 B2
(45) Date of Patent: Jan. 7, 2025

(54) BEHAVIORAL FEEDBACK SYSTEM FOR FACILITATING SHAPING A SUBJECT'S BEHAVIOR

(71) Applicant: Leonardo Junquera, South Salem, NY (US)

(72) Inventor: Leonardo Junquera, South Salem, NY (US)

( * ) Notice: Subject to any disclaimer, the term of this patent is extended or adjusted under 35 U.S.C. 154(b) by 921 days.

(21) Appl. No.: 17/218,395

(22) Filed: Mar. 31, 2021

(65) Prior Publication Data

US 2021/0307663 A1 Oct. 7, 2021

Related U.S. Application Data

(60) Provisional application No. 63/003,394, filed on Apr. 1, 2020.

(51) Int. Cl.
*G09B 19/00* (2006.01)
*A61B 5/11* (2006.01)
*A61B 5/16* (2006.01)
*A61B 5/00* (2006.01)

(52) U.S. Cl.
CPC .............. *A61B 5/16* (2013.01); *A61B 5/1118* (2013.01); *G09B 19/00* (2013.01); *A61B 5/0022* (2013.01); *A61B 5/681* (2013.01)

(58) Field of Classification Search
CPC ........... G09B 19/00; A61B 5/16; A61B 5/165; A61B 5/168
See application file for complete search history.

(56) References Cited

U.S. PATENT DOCUMENTS

| 6,039,688 A * | 3/2000 | Douglas | A61B 5/4866 600/300 |
| 8,137,108 B2 * | 3/2012 | Hamway | G09B 5/14 434/237 |
| 8,374,888 B2 * | 2/2013 | Earles | G16H 20/70 705/2 |
| 8,659,418 B2 * | 2/2014 | Kreml | A61B 5/1118 340/573.2 |

(Continued)

OTHER PUBLICATIONS

International Search Report for PCT/US2021/025079, dated Jun. 22, 2021 (2 pages).

*Primary Examiner* — Kurt Fernstrom
(74) *Attorney, Agent, or Firm* — Kevin P. Radigan, Esq.; Heslin Rothenberg Farley & Mesiti P.C.

(57) ABSTRACT

A behavioral feedback system is provided to facilitate shaping a subject's behavior during an activity by obtaining user input. The user input is obtained pursuant to user-selection of a behavior-related representation from a set of behavior-related representations, for an activity of a subject, displayed on an electronic device of the user. Each representation corresponds to a different potential behavior of the subject during the activity, and the selected behavior-related representation relates to a user-observed behavior of the subject during the activity. The method further includes determining, by one or more processors, a positive or negative feedback indication associated with the selected behavior-related representation, and generating a feedback signal to send to an electronic device of the subject to indicate to the subject the selected behavior-related representation and the associated positive or negative feedback indication.

13 Claims, 13 Drawing Sheets

(56) References Cited

U.S. PATENT DOCUMENTS

| | | | |
|---|---|---|---|
| 10,102,769 B2* | 10/2018 | Lacroix | G06F 16/284 |
| 10,909,867 B2* | 2/2021 | Benz | G09B 19/00 |
| 11,544,591 B2* | 1/2023 | Paulina | G16H 20/70 |
| 11,636,941 B2* | 4/2023 | Williams | G06Q 50/18 |
| | | | 705/2 |
| 2004/0010420 A1* | 1/2004 | Rooks | G16H 20/30 |
| | | | 705/2 |
| 2004/0131997 A1* | 7/2004 | McGuire | G09B 19/0092 |
| | | | 600/300 |
| 2005/0228692 A1* | 10/2005 | Hodgdon | G16H 10/40 |
| | | | 705/2 |
| 2006/0003305 A1* | 1/2006 | Kelmar | G09B 23/28 |
| | | | 434/350 |
| 2007/0054245 A1* | 3/2007 | Greenfield | G09B 5/14 |
| | | | 434/112 |
| 2008/0026349 A1 | 1/2008 | Verona | |
| 2009/0097757 A1 | 4/2009 | Wimsatt | |
| 2009/0191526 A1* | 7/2009 | Kumazawa | G09B 19/00 |
| | | | 434/238 |
| 2010/0035221 A1 | 2/2010 | O'Donnell | |
| 2010/0235776 A1* | 9/2010 | Brown | G06Q 10/10 |
| | | | 709/224 |
| 2011/0276369 A1 | 11/2011 | Bean et al. | |
| 2012/0244503 A1* | 9/2012 | Neveldine | G09B 19/00 |
| | | | 434/236 |
| 2012/0308970 A1 | 12/2012 | Gillespie et al. | |
| 2013/0216989 A1* | 8/2013 | Cuthbert | A61B 5/1113 |
| | | | 434/238 |
| 2014/0099614 A1* | 4/2014 | Hu | G09B 19/00 |
| | | | 434/236 |
| 2014/0127650 A1* | 5/2014 | Utter, II | G16H 20/60 |
| | | | 434/127 |
| 2015/0118667 A1* | 4/2015 | Andrew | G16H 40/63 |
| | | | 434/236 |
| 2015/0379880 A1* | 12/2015 | Sethi | G16H 20/70 |
| | | | 434/236 |
| 2017/0294137 A1 | 10/2017 | Khoury et al. | |
| 2017/0337839 A1* | 11/2017 | Yudofsky | G09B 5/00 |
| 2018/0012509 A1* | 1/2018 | Rose | G09B 19/0007 |
| 2018/0366024 A1* | 12/2018 | Yom-Tov | G06F 16/284 |
| 2019/0135177 A1* | 5/2019 | Farrell | B60Q 9/00 |
| 2019/0189025 A1 | 6/2019 | Angelopoulos et al. | |
| 2020/0152312 A1* | 5/2020 | Connor | G06V 20/20 |
| 2020/0235776 A1 | 9/2020 | Brown | |
| 2020/0345280 A1* | 11/2020 | AlShawoosh | G01R 33/20 |
| 2021/0104173 A1* | 4/2021 | Pauley | G16H 20/60 |
| 2021/0290131 A1* | 9/2021 | Kumar | A61B 5/1118 |
| 2022/0415476 A1* | 12/2022 | Connor | G06V 20/20 |

* cited by examiner

TOKENS/ICONS

POSITIVE BEHAVIORS:
1. ANSWERING QUESTIONS
2. RESPONDING
3. READING THE RIGHT WAY
4. FOLLOWING ALONG WITH CLASSMATES WHEN READING
5. CALM BODY (QUIET HANDS, SITTING UP, EYES OPEN)
6. WRITING NEATLY
7. VOICE VOLUME
8. APPROPRIATE PACE
9. NOT INTERRUPTING/SAY EXCUSE ME
10. WORK WITH PARTNER
11. INITIATING AND ON TOPIC
12. FOCUSED
13. STOP & THINK
14. LOOKING AT WHO IS TALKING
15. USING MANNERS
16. GIVING PERSONAL SPACE
17. LOOKING BACK AT TEXT
18. FEET UNDER CHAIR
19. WAITING FOR TURN
20. TALK NICELY
21. SANITARY BEHAVIOR
22. SHUT CABINETS

NEGATIVE BEHAVIORS:
1. LAUGHING (WHILE WORKING)
2. INAPPROPRIATE COMMENTS (CURSING, COPYING PEERS, COMPLAINING)
3. NON-COMPLIANCE
4. NOT ANSWERING QUESTIONS/RESPONDING
5. NOT ASKING FOR PERMISSION (REPETITIVE BEHAVIORS)
6. YELLING
7. WHINING
8. NO CALM BODY
9. SCRIPTING WHILE WORKING
10. NOT FOCUSED
11. OFF TASK
12. STARING AT PEOPLES CLOTHING
13. KARATE AT THE WRONG TIME/KARATE FISTS
14. TOO CLOSE TO PEOPLE/TOUCHING OTHER PEOPLE, BUMPING INTO PEOPLE IN KITCHEN (PERSONAL SPACE)
15. CALLING TEACHERS BY THEIR FIRST NAMES
16. STOPPING AND LOOKING IN CLASSROOMS WHILE TEACHER IS TEACHING
17. UNSANITARY BEHAVIORS
18. WINKING AT A LIGHT

FIG 3

RECEIVING A USER-INDICATION OF INITIATION OF AN OBSERVATION SESSION FOR THE ACTIVITY OF THE SUBJECT;

BASED ON RECEIVING THE INDICATION, CREATING A SESSION DATA STRUCTURE IDENTIFYING ONE OR MORE BEHAVIOR-RELATED REPRESENTATIONS OF THE SET OF DEFINED BEHAVIOR-RELATED REPRESENTATIONS FOR THE ACTIVITY OF THE SUBJECT; AND

LOGGING THE SELECTED BEHAVIOR-RELATED REPRESENTATION AND THE TOKEN SCORE IN THE SESSION DATA STRUCTURE FOR THE OBSERVATION SESSION — 916

REPEATING THE METHOD FOR A PLURALITY OF OBSERVATION SESSIONS AND SAVING SESSION DATA STRUCTURES FOR THE PLURALITY OF OBSERVATION SESSIONS IN A DATABASE FOR TRACKING USER-OBSERVED BEHAVIOR OF THE SUBJECT ACROSS THE PLURALITY OF OBSERVATION SESSIONS FOR ONE OR MORE ACTIVITIES OF THE SUBJECT — 918

PREDEFINING THE SET OF DEFINED BEHAVIOR-RELATED REPRESENTATIONS FOR THE SUBJECT AND THE ACTIVITY FROM A LARGER GROUP OF DEFINED BEHAVIOR-RELATED REPRESENTATIONS SELECTABLE FOR INCLUSION IN THE SET OF DEFINED BEHAVIOR-RELATED REPRESENTATIONS, AND ASSOCIATING A RESPECTIVE TOKEN SCORE WITH EACH DEFINED BEHAVIOR-RELATED REPRESENTATION IN THE SET OF DEFINED BEHAVIOR-RELATED REPRESENTATIONS — 920

WHERE THE ACTIVITY IS ONE DEFINED ACTIVITY OF A PLURALITY OF DEFINED ACTIVITIES FOR THE SUBJECT, AND WHEREIN THE METHOD FURTHER INCLUDES OBTAINING A RESPECTIVE SET OF DEFINED BEHAVIOR-RELATED REPRESENTATIONS FOR EACH DEFINED ACTIVITY OF THE SUBJECT OF THE PLURALITY OF DEFINED ACTIVITIES, WHERE AT LEAST TWO RESPECTIVE SETS OF DEFINED BEHAVIOR-RELATED REPRESENTATIONS OBTAINED FOR AT LEAST TWO DIFFERENT DEFINED ACTIVITIES INCLUDE ONE OR MORE DIFFERENT DEFINED BEHAVIOR-RELATED REPRESENTATIONS FOR THE DIFFERENT DEFINED ACTIVITIES OF THE SUBJECT — 922

WHERE THE ELECTRONIC DEVICE OF THE SUBJECT IS A WEARABLE ELECTRONIC DEVICE ASSOCIATED WITH THE SUBJECT, AND THE METHOD FURTHER INCLUDES: RECEIVING A USER-INDICATION OF INITIATION OF AN OBSERVATION SESSION FOR THE ACTIVITY OF THE SUBJECT

RECEIVING BIOMETRIC DATA OF THE SUBJECT DURING THE ACTIVITY, THE BIOMETRIC DATA BEING OBTAINED VIA THE WEARABLE ELECTRONIC DEVICE MONITORING THE SUBJECT DURING THE ACTIVITY

SAVING THE SELECTED BEHAVIOR-RELATED REPRESENTATION AND THE BIOMETRIC DATA IN A SESSION DATA STRUCTURE FOR THE OBSERVATION SESSION — 924

FIG. 9B

BEHAVIORAL FEEDBACK SYSTEM FOR FACILITATING SHAPING A SUBJECT'S BEHAVIOR

CROSS-REFERENCE TO RELATED APPLICATIONS

This application claims the benefit of U.S. provisional patent application Ser. No. 63/003,394, filed Apr. 1, 2020, entitled "Wearable Behavior Token Delivery and Tracking System", which is hereby incorporated herein by reference in its entirety.

BACKGROUND

Shaping behavior of a subject with autism or other behavioral challenges across activities or environments (school, home, community, etc.) by different users or caretakers (therapists, teachers, parents, etc.) while fostering independence is very challenging. Interventions typically require cumbersome equipment (pens, paper, clipboards), data collection can be difficult and is frequently discarded, and informing the subject of the positive/negative behavior can be disruptive requiring a 1:1 therapist next to the patient at all times. This can be stigmatizing, particularly during many normal activities.

SUMMARY

Certain shortcomings of the prior art are overcome and additional advantages are provided through the provision of a method, which includes obtaining user input data, the user input data being obtained for an activity of a subject, at least in part, pursuant to user-selection of a behavior-related representation from a set of defined behavior-related representations displayed on an electronic device of the user. Each defined behavior-related representation corresponds to a different potential behavior of the subject during the activity, and the selected behavior-related representation relates to a user-observed behavior of the subject during the current activity. The method further includes: determining, by one or more processors, a positive or negative feedback indication associated with the selected behavior-related representation; and generating a feedback signal to send to an electronic device of the subject to indicate to the subject the selected behavior-related representation and the associated positive or negative feedback indication, where the feedback signal is generated to assist the subject in shaping the subject's behavior. Advantageously, the behavioral feedback method, system and computer program product disclosed assists a user or caretaker in shaping behavior of a subject. The method, system and computer program product disclosed provide a non-intrusive facility for real-time feedback to a subject, with minimal disruption in the activity of the subject, to facilitate shaping the subject's behavior.

In one example, the set of defined behavior-related representations includes one or more defined behavior-related representations corresponding to one or more positive behaviors of the subject for the activity, and one or more defined behavior-related representations corresponding to one or more negative behaviors of the subject for the activity. The facility disclosed advantageously allows for providing positive feedback for one or more positive behaviors of the subject during the activity, and/or for indicating one or more negative behaviors of the subject during the activity.

In another example, the method further includes ascertaining a token score for the selected behavior-related representation. In one example, each defined behavior-related representation of the set of defined behavior-related representations has a respective token score associated therewith for the activity of the subject. By associating a token score with each defined behavior-related representation, a user can customize the behavioral feedback facility for a particular subject.

In one embodiment, the set of defined behavior-related representations and respective token scores are user-modifiable, and the method further includes receiving a user-modification to the set of defined behavior-related representations and respective token scores for the activity of the subject, the user-modification including one or more of adding, editing or deleting a behavior-related representation or a token score of the set of defined behavior-related representations and respective token scores. Advantageously, the behavioral feedback facility disclosed allows for a user-modification of the set of defined behavior-related representations and respective token scores for the activity of the subject, allowing customization of the set of defined behavior-related representations and/or respective token scores for the respective subject and/or activity, as well as for adjustment of behavior-related representations or respective token scores as the subject progresses in the activity, as well as to emphasize certain positive or negative behaviors.

In one implementation, the method further includes receiving a user-indication of initiation of an observation session for the activity of a subject, and based on receiving the indication, creating a session data structure identifying one or more behavior-related representations of the set of defined behavior-related representations for the activity of the subject, and logging the selected behavior-related representation and the token score in the session data structure for the observation session.

In one example, the method further includes repeating the method for a plurality of observation sessions, and saving session data structures for the plurality of observation sessions in a database for tracking user-observed behavior of the subject across the plurality of observation sessions for one or more activities of the subject. Advantageously, by logging multiple session data structures for multiple observation sessions, the collected data can be used to track progress of the subject over multiple sessions, as well as to share session data with, for instance, other individuals assisting with the subject's care. Additionally, the aggregate data can be shared with one or more researchers, from which conclusions about the subject, as well as the behavioral facility, can be drawn, helping to improve behavior-shaping techniques. Further, insights from these conclusions can be shared with the overall community, as well as specific data contributors.

In one example, the method further includes predefining the set of defined behavior-related representations for the subject and the activity from a larger group of defined behavior-related representations selectable for inclusion in the set of defined behavior-related representations, and associating a respective token score to each defined behavior-related representation in the set of defined behavior-related representations.

In one embodiment, the activity is one defined activity of a plurality of defined activities for the subject, and wherein the method further includes obtaining a respective set of defined behavior-related representations for each defined activity of the subject of the plurality of defined activities, where at least two respective sets of defined behavior-related representations obtained for at least two different defined activities include one or more different defined behavior-related representations for the different defined activities of the subject.

In another example, the electronic device of the subject is a wearable electronic device associated with the subject, and the method further includes receiving a user-indication of initiation of an observation session for the activity of the subject, and receiving biometric data of the subject during the activity, the biometric data being obtained via the wearable electronic device monitoring the subject during the activity, and saving the selected behavior-related representation and the biometric data in a session data structure for the observation session.

Systems and computer program products corresponding to the above-summarized methods are also described and claimed herein. Further, services relating to one or more aspects are also described and may be claimed herein.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed at the conclusion of the specification. The foregoing and other objects, features, and advantages of the invention are apparent from the following detailed description taken in combination with the accompanying drawings in which:

FIG. 3 depicts example tokens and positive and negative behaviors of one embodiment of a set of defined behavior-related representations, in accordance with an aspect of the present invention;

FIGS. 9A-9B depict one example of processing within a behavioral feedback system, in accordance with one or more aspects of the present invention.

DETAILED DESCRIPTION

Figure 1:
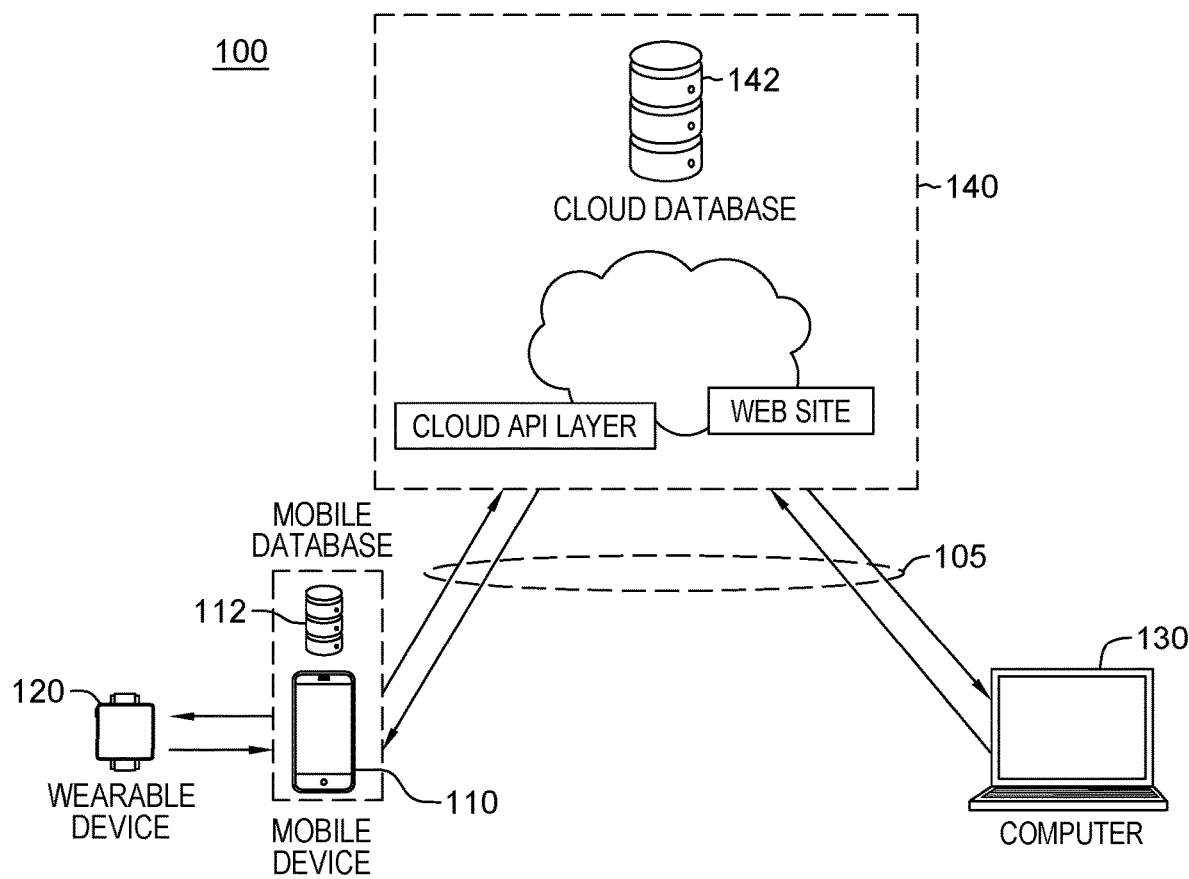
FIG. 1 depicts a high level architecture embodiment of a system, in accordance with one or more aspects of the present invention.

In one or more embodiments the present invention comprises a technique, method, and system with associated program products for helping caretakers shape behaviors in subjects, collect data, track data, and share data, in a convenient non-intrusive manner, using (for instance) a mobile application, a wearable device, and cloud-based processing or storage. It also enables new opportunities for identifying and sharing activity and behavior configurations, which others can utilize in their implementations. Additionally, the aggregate data can be shared with researchers from which conclusions about token economies can be drawn, helping to improve behavior shaping techniques. Insights from these conclusions can be shared with the overall community, as well as specific data contributors.

In one embodiment, a user defines a set of behaviors, both positive (ones to encourage) and negative (ones to discourage), in the mobile application. The behaviors can be assigned names and icons, or images, representing the behavior. The user can add, edit, or delete the behaviors.

In one embodiment, the user defines a list of activities representing the environments, scenarios, or circumstances under which they want to utilize the system. Example activities include: school, cooking, shopping, driving, sport lessons, karate lessons, etc. The user will assign a list of behaviors from the list of behaviors which they previously defined and assign points or scores to them for that activity. Positive numbers for behaviors to encourage and negative numbers for behaviors to discourage. In one embodiment, all behaviors, activities, and icons are stored on the mobile device and can (depending on the type of license the user has) be saved to a database of cloud-based resources as well. The activities can be edited or deleted as well.

In one embodiment, the subject will wear a wearable device (a smartwatch such as an iWatch™ or Wear OS™ device), while the user holds the mobile device. The user will run the activity configuration, previously defined to display a list of the behaviors for that activity, along with the points they associated with them. When the user sees one of the behaviors, they will select the corresponding behavior representation from the list. In one embodiment, the wearable device will vibrate, indicating to the subject they either gained or lost points (different vibrations for each). The icon or image associated with that behavior will also appear on the watch, relaying to the subject what behavior was exhibited. This will continue until the user ends the observation session for the selected activity. In one example, all behaviors will be recorded on the device, along with the points. The intent is that the subject will earn rewards based on the number of points they receive. The higher number of points the more desirable rewards will be given. The lower number of points the less desirable rewards will be given.

In one embodiment, the data from the activity runs will be stored in the cloud and can be sharable with team members. Based on the type of license the user has, the data can be replicated or archived to the cloud. Depending on the permissions the user configures, the data can also be shared.

In one embodiment, the de-personalized data from the user, uploaded to the cloud, will be anonymously shared with researchers who own a license, for the purpose to draw insights on token economies. Age and gender information may be included along with the log of each token event and each session.

In one embodiment, additional information such as heart rate can be collected, stored, and synced with the cloud to see if there is a correlation between the behavior data and the biometric information to determine if there is predictive capability for behavioral data.

In one embodiment, there is a companion mobile application to view a subject's historical data, current activities in progress, receive alerts, and configure access to the subject's data.

In one embodiment, there is a configuration under which a user can utilize the mobile application and wearable device across multiple subjects. In this configuration, the user will have the proper license to support multiple subjects and will define and run activities for each subject. The data will be categorized by subject on the device, and in the cloud, provided the user has the proper license and the subject's data is configured for cloud storage.

In one embodiment, the caretaker or user will select an image of a reward (example, a bag of potato chips) on their mobile app which would get sent down to the subject's wearable device, which would indicate through a vibration that a session had started. The image would be black and white and divided into a number of parts representing tokens (example 9 tokens, a three by three grid). As the subject displayed positive behaviors, the caretaker would use the mobile app to initiate a token be sent to the subject. The next box in the grid would turn from black and white to a color, indicating a token had been earned. Tokens can be taken away by the caretaker, through the mobile app, due to undesired behavior in the subject. When all grids of the image are in color, the reward will be earned by the subject and they will receive the reward.

In one embodiment, tokens will be letters used to spell out a word, which represents a reward. The word will be entered into the mobile app and appear on the wearable, either seeded with a token letter, or not, in a faded format. The seeded letter will be brighter or a different color from the others. When the subject earns a token or tokens, the caretaker will press a button on the mobile, the wearable will vibrate, and the next letter will light up. The caretaker can also remove tokens for undesired behaviors. The wearable will vibrate in this circumstance, and the letter will become faded again. When the word is complete, the subject earns the reward spelled out on the wearable.

In one embodiment, a self-management module will allow the caretaker or user to initiate a scenario or activity and allow the subject to respond as to their compliance with the behaviors. A timer will be used on the app to send questions regarding the subject's compliance with a given behavior or set of behaviors on a regular interval (e.g. "do you have a quiet body?"). The subject will also be presented with "yes" and "no" buttons and will respond. Based on their response they will get points or tokens. When the program time has run out, the subject will be notified if they earn the reward or not. All data will be tracked in the local database and, depending on the license type, will be synchronized with a cloud-based database.

In one embodiment, the capability for a caretaker or user to deliver a token remotely to the wearable device is supported. This use case supports remote scenarios or activities where the caretaker is in another location but viewing and communicating with the subject through another service (e.g. Skype, Zoom, etc.) The caretaker can observer behaviors and send positive/negative feedback which will initiate a process on the wearable device, issuing or revoking a token. All data will be recorded and tracked on the user's mobile device and in the cloud.

By way of example, FIG. 1 depicts a high-level architecture embodiment of a system 100, in accordance with one or more aspects of the present invention. In the embodiment depicted, system 100 includes a user electronic device 110, such as a mobile phone or other mobile electronic device, and an electronic device 120 associated with a subject, such as a wearable electronic device. In the embodiment illustrated, electronic device 110 includes associated storage 112 for, for instance, storing program code configured to implement one or more aspects described herein, as well as to store session data on one or more user-implemented observation sessions for the subject. In one embodiment, user electronic device 110 and subject electronic device 120 are in wireless communication.

In the embodiment of FIG. 1, system 100 further includes one or more networks 105 across which user electronic device 110 can be in operative communication with cloud-based computing resource(s) 140, with cloud-based storage 102 and/or one or more remote computer systems 130 for, for instance, remote monitoring of observation session data by user electronic device 110. As illustrated, in one embodiment, user electronic device 110 can communicate across network(s) 105 with cloud-based computing resource(s) 140 via a cloud API layer, and computer system(s) 130 can communicate across network(s) 105 with cloud-based computing resource(s) 140 via one or more websites, in one example.

Figure 2:
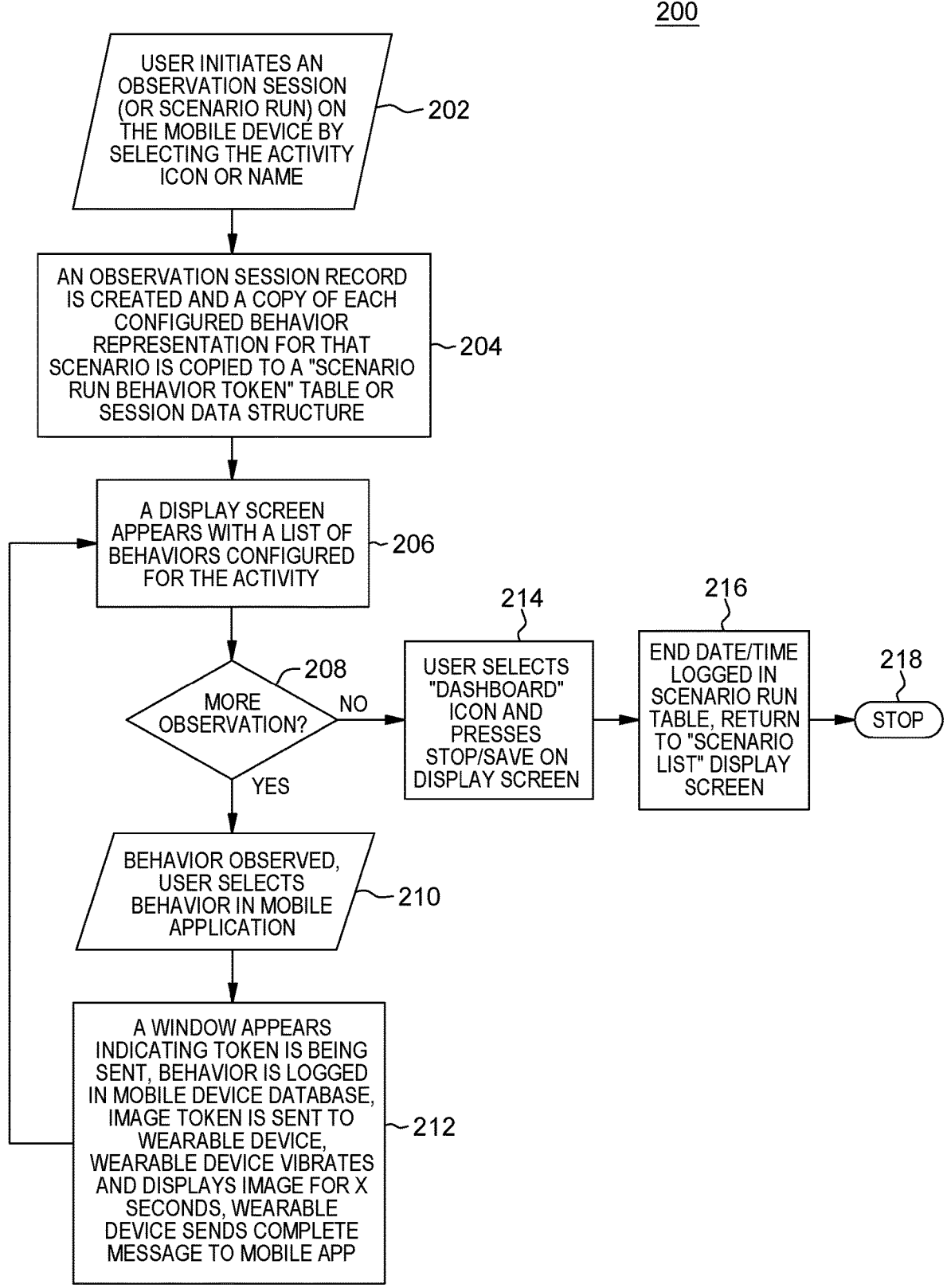
FIG. 2 depicts one embodiment of a behavior session process flow, in accordance with one or more aspects of the present invention.

FIG. 2 depicts one embodiment of a behavior or observation session process flow, in accordance with one or more aspects of the present invention. As illustrated, process 200 includes a user initiating an observation session (or scenario run) on the user's electronic device by clicking or otherwise selecting an icon representative of the scenario or activity name 202. An observation session record (or scenario run record) is then created, and in one embodiment, a copy of each defined behavior-related representation for that activity is copied to a session data structure, also referred to as a scenario run behavior token table 204.

In one embodiment, a display screen appears on the user's electronic device with a list of defined behavior-related representations configured for the activity (or scenario) 206. The observation session begins and the user observes the subject during the activity 208. During observation, the user may observe a behavior on the list of defined behavior-related representations, and click or otherwise select the defined behavior-related representation in the user's electronic device 210. In one embodiment, a window, or dialog box, appears, indicating a token is being sent to the subject, and the behavior representation is logged in the user's electronic device. Further, an image token can be sent to the subject's electronic device, and in one embodiment, the subject's electronic device can vibrate and display an image for a defined time interval. Further, the subject's electronic device can send a completed message to the user's electronic device once finished 212. Once the observation session completes, the user's electronic device can present the user with a display that allows the user to stop and/or save session-related data 214. The ending day and time can also be logged into the session data structure, and the user's electronic device can return to the activity list display screen 216, which completes 218 the session process flow embodiment.

By way of example, FIG. 3 illustrates example tokens or icons and positive and negative behaviors associated therewith for one embodiment of a set of defined behavior-related representations. In one implementation, the defined behavior-related representations can be a master set of defined behavior-related representations from which certain representations are selected by the user when creating a particular list or set of defined behavior-related representations for a specified activity of the subject. For instance, a particular activity may only have a subset of the defined behavior-related representations illustrated associated therewith. In one implementation, the set is user-defined, and can be dynamically modified by the user to add, edit or delete representations in a list of defined behavior-related representations for a particular activity of the subject when desired. In implementation, the behaviors and associated tokens or icons of each behavior would be reviewed with the subject ahead of time so that during the activity, the subject is aware of the particular behavior when the associated token or icon is displayed on the subject's electronic device.

Figure 4:
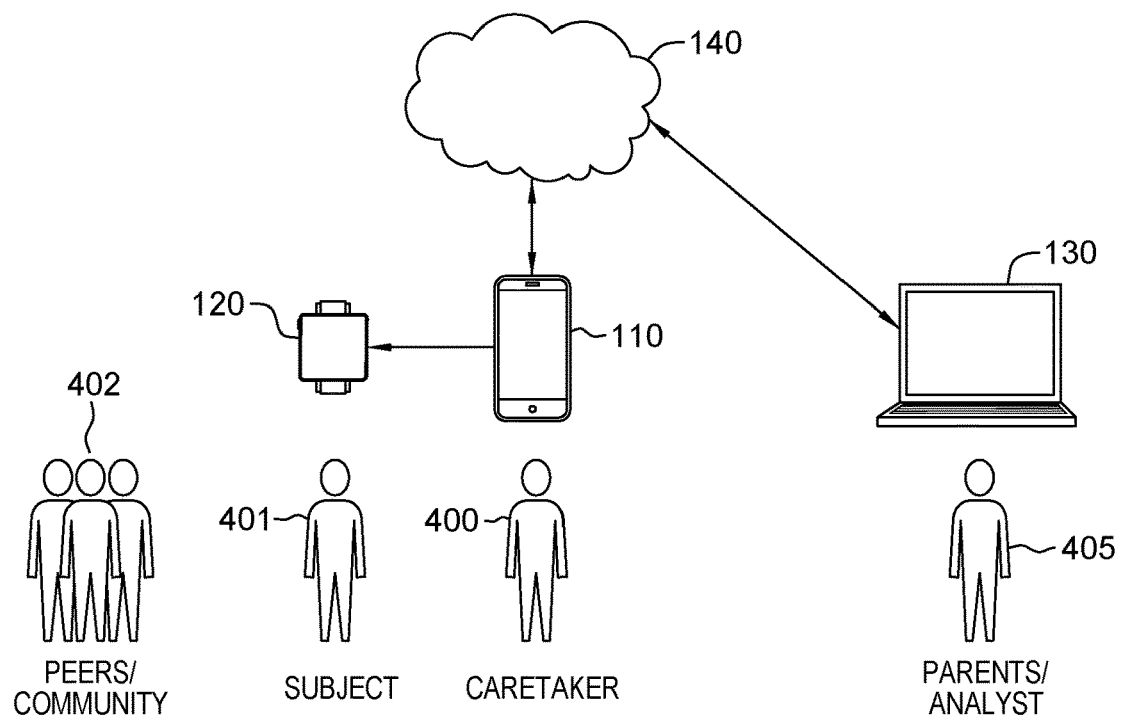
FIG. 4 depicts an example usage diagram—direct scenario, in accordance with an aspect of the present invention.
Figure 5:
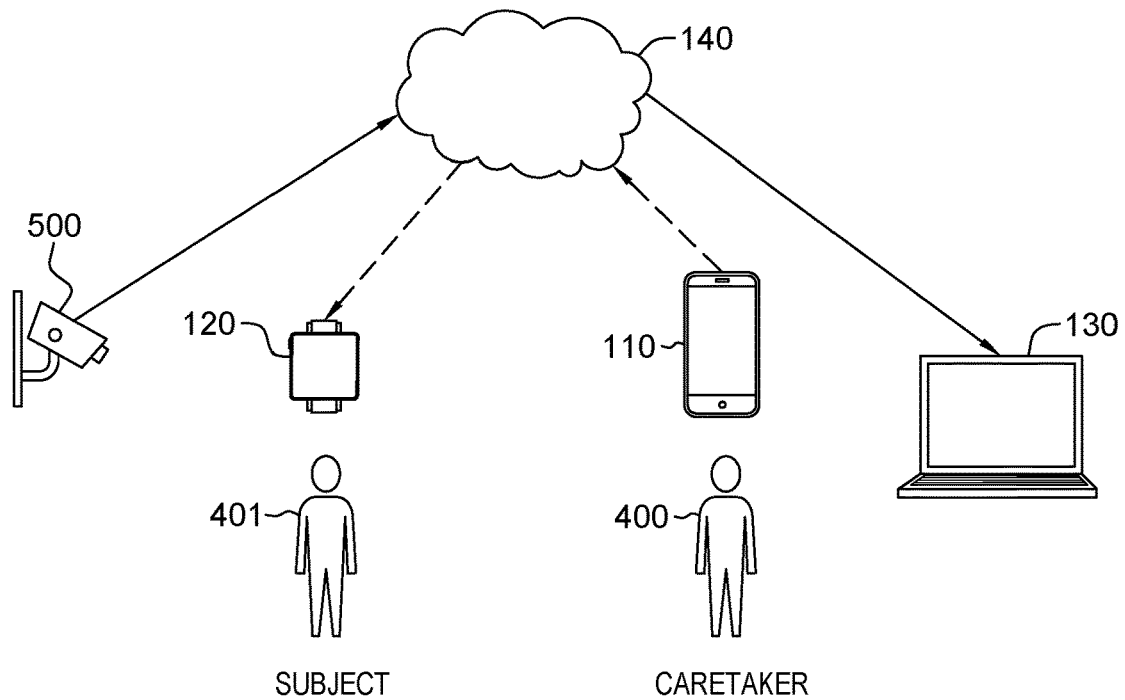
FIG. 5 depicts an example usage diagram—remote scenario, in accordance with an aspect of the present invention.

FIGS. 4 & 5 depict different usage examples of a system, in accordance with one or more aspects of the present invention.

In FIG. 4, the system includes user electronic device 110, such as an electronic device of a caretaker 400, and the subject's electronic device 120, such as a wearable electronic device or another mobile device associated with the subject 401. In one embodiment, the wearable electronic device can be, for instance, one or more of a wearable smartwatch, smartglasses, Internet of Things (IoT) devices, etc. In this example, subject 401 can be participating in an activity with the subject's peers or community 403, and is being observed by caretaker 400, with the caretaker using the behavioral feedback system described herein to facilitate assisting subject 400 in shaping the subject's behavior during the activity. In the embodiment illustrated, user electronic device 110 can be in communication with cloud-based computing resource(s) 140 to, for instance, allow a parent or analyst 405 located remotely from subject 401 to monitor (via computer system 130) the subject's progress during the activity, and/or to review session-related data generated through use of the behavioral feedback system described.

In the example of FIG. 5, the behavioral feedback system is used in a remote scenario, where the user, for instance, caretaker or caregiver 400, is located remote from subject 401, and is monitoring the subject via one or more feedback systems 500, such as one or more cameras providing video of the subject 401 during the activity. In one example, the video is provided back via a cloud-based computing resource(s) 140 to the user (e.g., caretaker 400), and in particular, to the user's electronic device 110 and/or other computer system 130, such as a laptop computer, desktop computer, workstation, etc. Caretaker 400 (in this scenario) monitors the user remotely via the video feed 500, and when a behavior to be noted is observed, user electronic device 110 or computer system 130 is used to select a defined behavior-related representation and send a feedback signal to the subject's electronic device 120 as described herein. Note that other direct and remote scenarios in addition to those depicted in FIGS. 4 & 5 are possible using a behavioral feedback system, method and computer program product, as described herein. Note also that, as used herein, electronic device refers to any electronic device, system or computing resource implementing, at least in part, the behavioral feedback system disclosed herein. For instance, in one embodiment, electronic device can refer to the user's electronic device 110, or to computer system 130, or other computing resource, such as cloud-based computing resource(s) 140, depending on the aspect described.

Figure 6B:
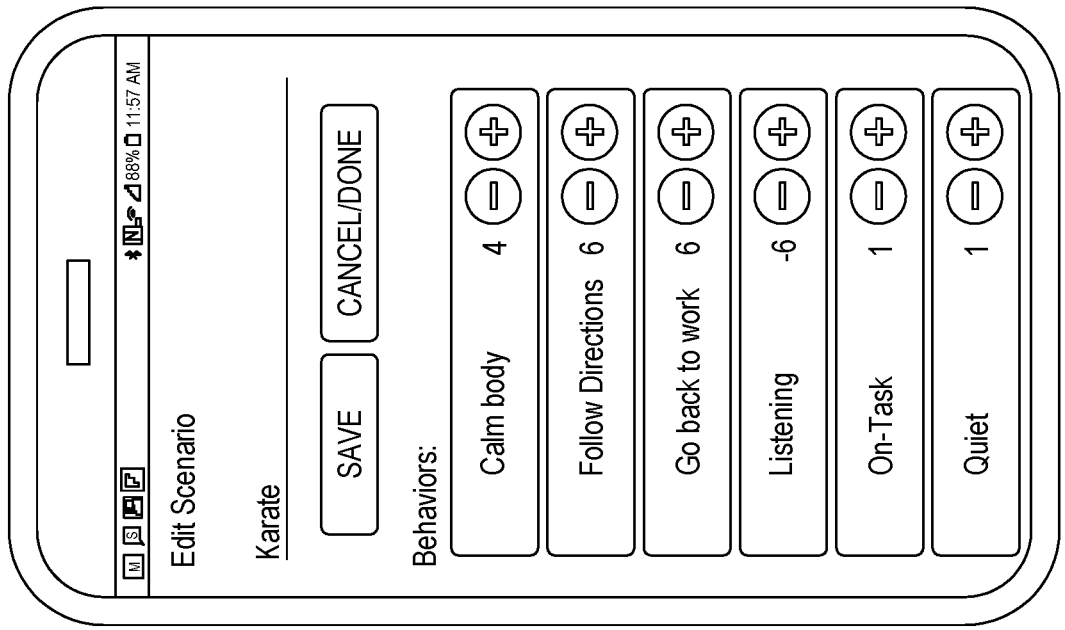
FIGS. 6A-6H depict a series of screenshots representing one or more embodiments of the user interface components of the user's electronic device and the subject's electronic device, in accordance with an aspect of the present invention.
Figure 6A:
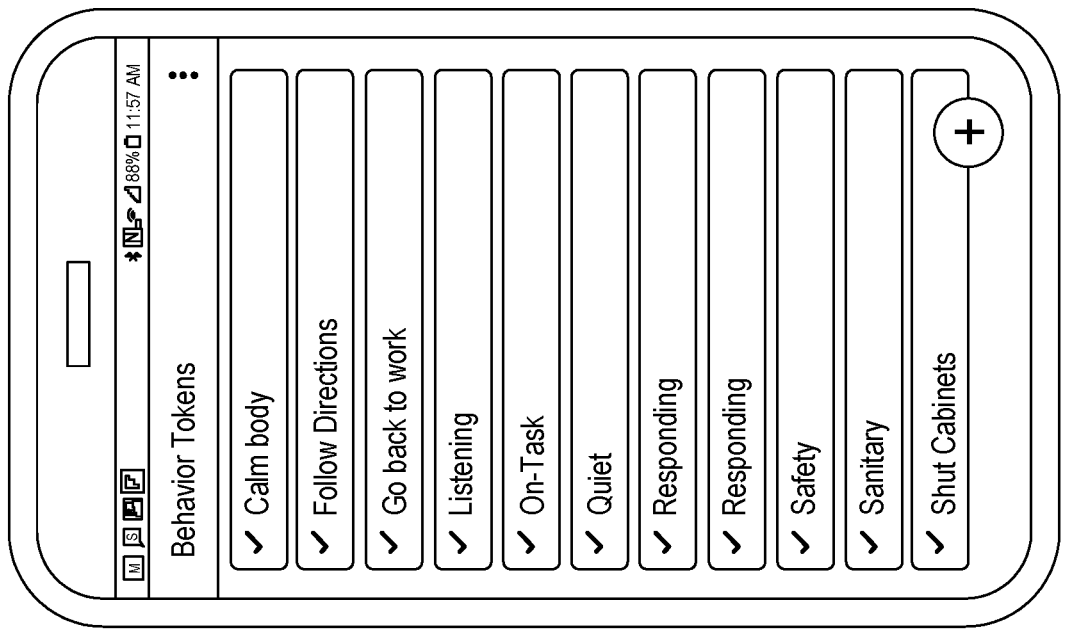

In one embodiment, the user can be the subject's father, who may take his autistic son to a karate lesson where he has had a number of interfering stereotypies. These might include winking at the lights, continually tightening his belt, pretending to pick up something from the ground, and making faces in the mirror. All of these behaviors interfere with his ability to learn and participate. With reference to the images of FIGS. 6A-6H, the user creates a list of negative behaviors in the mobile application, as well as a number of positive behaviors (FIG. 6A) to learn such as calm body, quiet mouth, and paying attention. The user would create an activity (or a scenario) named "karate" in the mobile application and add the defined behaviors to the activity. The user can also assign the stereotypical behaviors negative points and assign the behaviors that he is looking to encourage positive points (FIG. 6B). The parent (or user) teaches his son what the icons represent and that he would earn something he wanted, such as a karate t-shirt, if he earned a set number of points. The desired and undesired behaviors may be taught outside of this application.

Figure 6D:
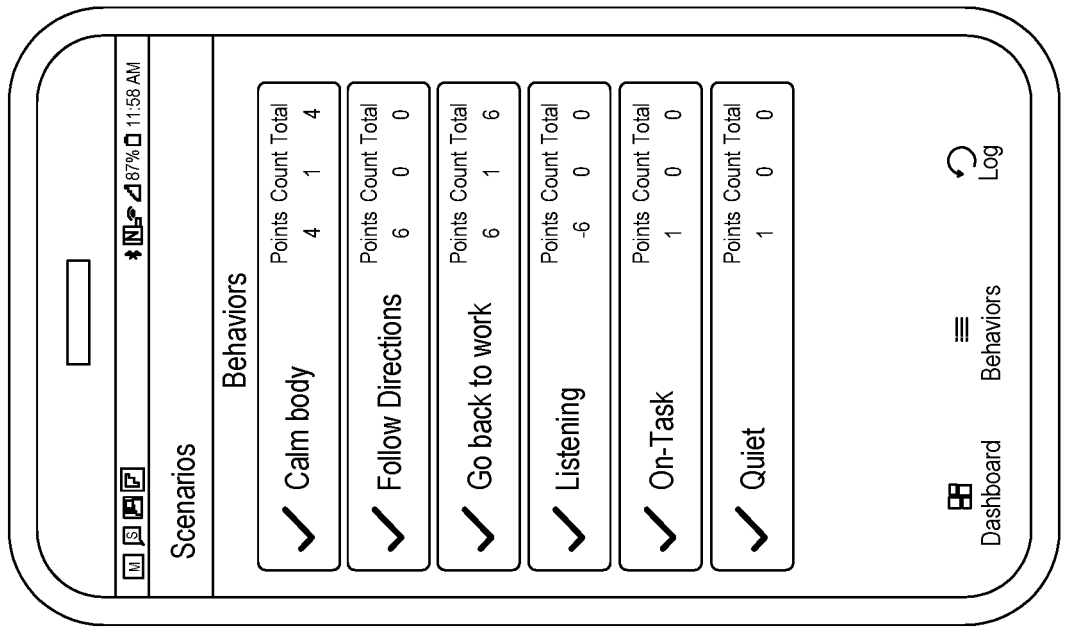
Figure 6C:
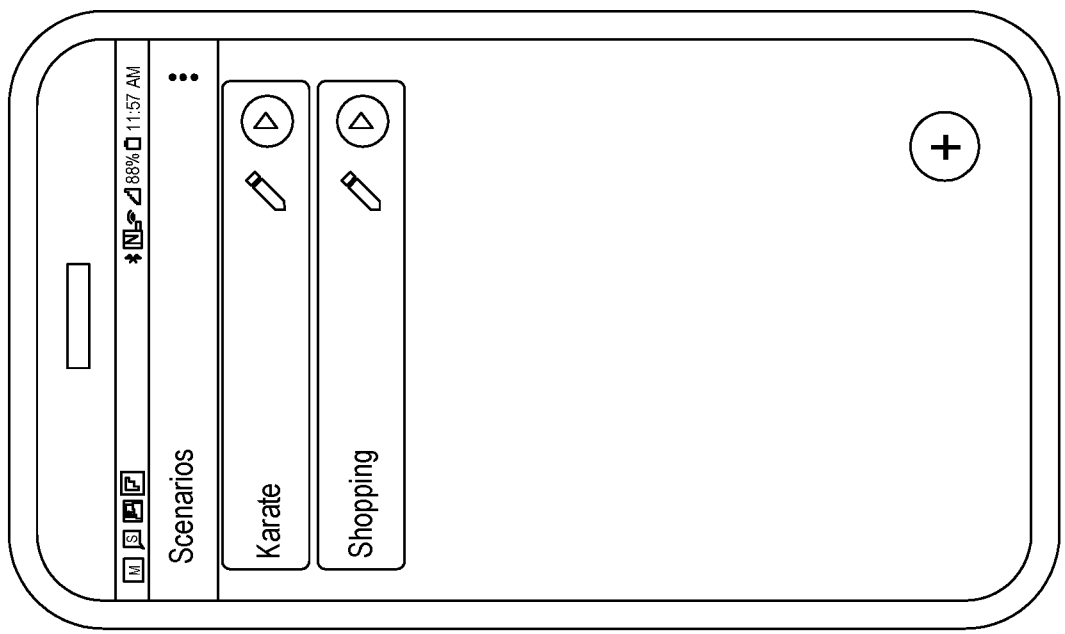
Figure 6F:
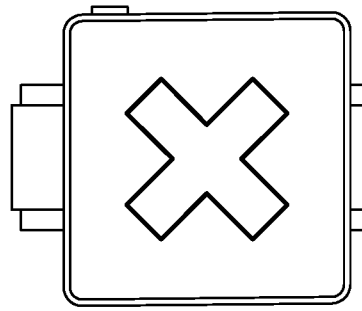
Figure 6G:
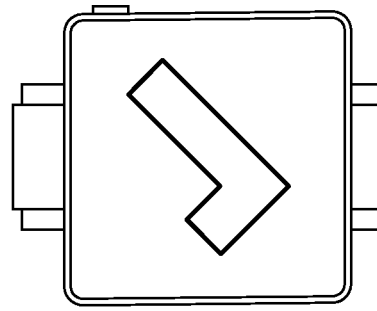
Figure 6E:
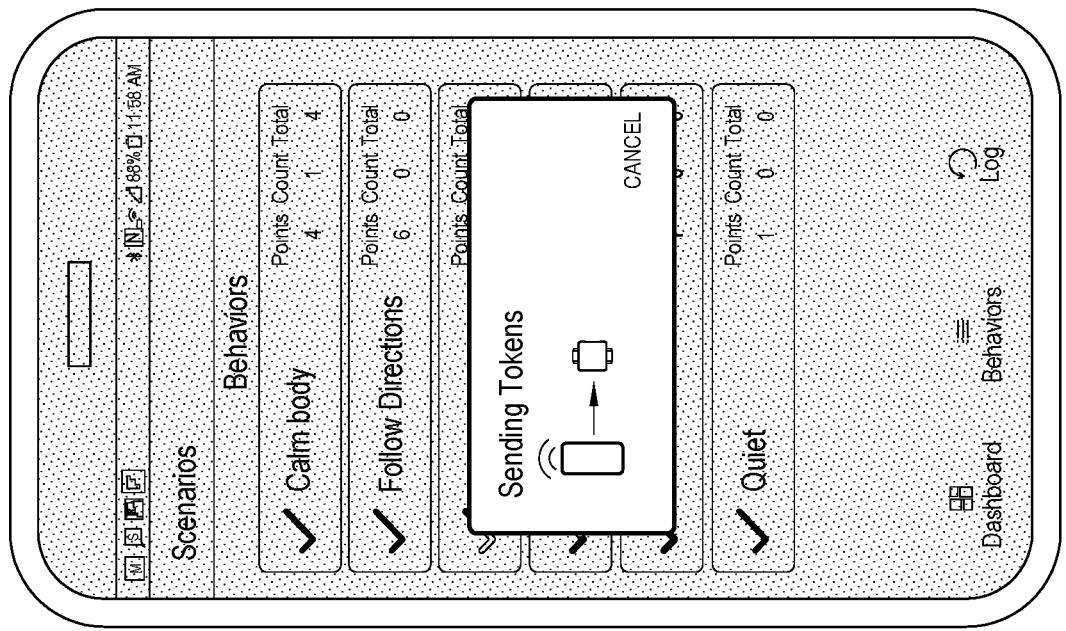

In the next karate lesson, the subject wears the smart watch, and the user would stand outside the session and observe him, holding the mobile application. The user starts the karate activity (FIG. 6C) on the mobile app and watches for the behaviors. If the user sees the subject not following directions, the user clicks on that behavior representation in the list (FIG. 6D). The mobile sends the feedback signal with the associated icon (FIG. 6E) to the subject's wearable device, and it would vibrate (FIG. 6F) in one embodiment. Thus, the subject can then look at the wearable device (i.e., a smartwatch) and see what behavior icon was sent and understand that points were taken. The user does the same for other behaviors, trying to focus on positive ones (FIG. 6G), throughout the lesson.

Figure 6H:
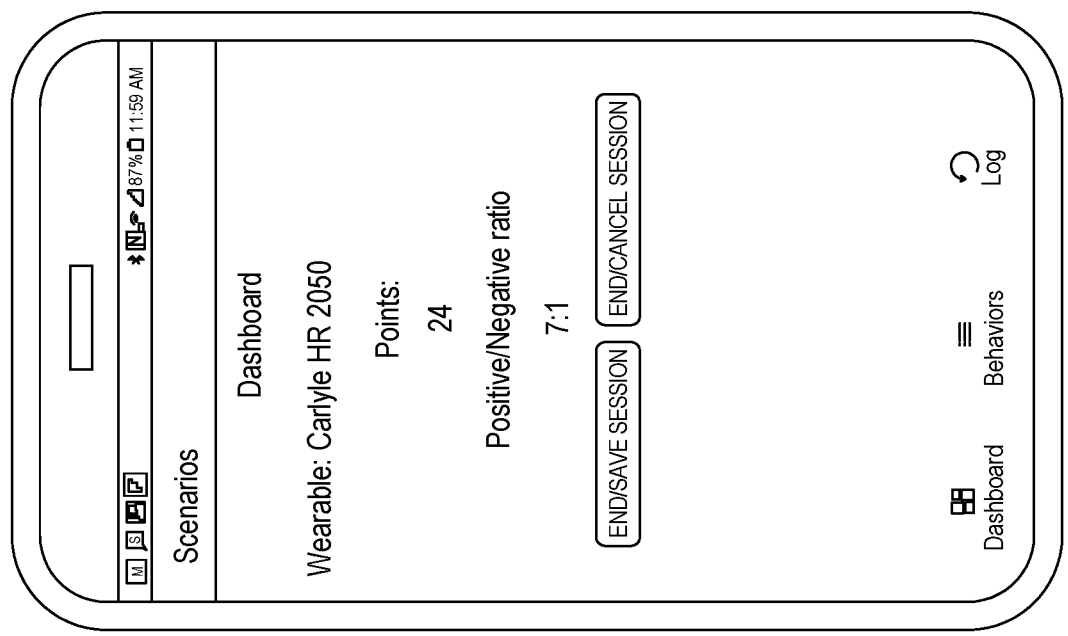

When the lesson is over, the user can show the subject how many points he earned on the mobile application (FIG. 6H). If he earned (for instance) 20 points or more, the user might allow the subject to get a karate t-shirt. This method increases the subject's independence, as the user does not need to be in the karate session with him reminding him of what he should or should not do.

The data from the karate lesson session can be uploaded to a database, such as a cloud-based database, where the subject's parents, caregivers, analysts', etc., can review the results, and all other activity sessions to see progress or identify challenges.

As understood by one skilled in the art from the description provided, a system, computer-implemented method, and program product are disclosed herein for a behavioral feedback facility for assisting in shaping a subject's behavior. Embodiments of the present invention include a computer-implemented method, a system and a computer program product, where program code executing on one or more processors obtains user input data (such as on an electronic device of a user), where the user input data is obtained for an activity of a subject, at least in part, pursuant to user-selection of a behavior-related representation from a set of defined behavior-related representations displayed on the user's electronic device. Each defined behavior-related representation corresponds to a different potential behavior of the subject during the activity. The selected behavior-related representation relates to a user-observed behavior of the subject during the activity. Embodiments of the present invention further include program code to determine, by one or more processors, a positive or negative feedback indication associated with the selected behavior-related representation, and to generate a feedback signal to send to an electronic device of the subject to indicate to the subject the selected behavior-related representation and the associated positive or negative feedback indication. The feedback signal is generated to assist in shaping the subject's behavior.

In one or more embodiments, the set of defined behavior-related representations includes one or more defined behavior-related representations corresponding to one or more positive behaviors of the subject for the activity, and one or more defined behavior-related representations corresponding to one or more negative behaviors of the subject for the activity.

In one or more implementations, the method further includes ascertaining a token score for the selected behavior-related representation. Further, in one or more embodiments, each defined behavior-related representation of the set of defined behavior-related representations has a respective token score associated therewith for the activity of the subject.

In certain embodiments, the set of defined behavior-related representations and respective token scores are user-modifiable, and the method further includes receiving a user-modification to the set of defined behavior-related representations and respective token scores, for the activity of the subject, the user-modification including one or more of adding, editing or deleting a behavior-related representation or a token score of the set of defined behavior-related representations and respective token scores.

In one or more embodiments, the method further includes receiving a user-indication of initiation of an observation session for the activity of the subject, and based on receiving the indication, creating a session data structure identifying one or more behavior-related representations of the set of defined behavior-related representations for the activity of the subject, and logging the selected behavior-related representation and associated token score in the session data structure for the observation session.

In one embodiment, the method is repeated for a plurality of observation sessions, and session data structures for each observation session is saved in a database for tracking user-observed behavior of the subject across the plurality of observation sessions for one or more activities of the subject.

In one example, the set of defined behavior-related representations are predefined for the subject and the activity from a larger group of defined behavior-related representations selectable (e.g., by the user) for inclusion in the set of behavior-related representations, and associating a respective token score to each defined behavior-related representation in the set of defined behavior-related representations.

In one or more embodiments, the activity is one defined activity of a plurality of defined activities for the subject, and the method includes obtaining a respective set of defined behavior-related representations for each defined activity of the subject of the plurality of defined activities, where at least two respective sets of defined behavior-related representations obtained for at least two different defined activities include one or more different defined behavior-related representations for the different defined activities of the subject.

In one or more embodiments, the electronic device of the subject is a wearable electronic device associated with the subject, such as a smartwatch or smartglasses. In one embodiment, the method further includes receiving a user-indication of initiation of an observation session for the activity of the subject, and receiving biometric data of the subject during the activity, the biometric data being obtained via the wearable electronic device monitoring the subject during the activity. Further, the method includes saving the selected behavior-related representation and the biometric data in a session data structure for the observation session.

Embodiments of the present invention are inextricably tied to computing and advantageously constitute an unconventional and unique combination of elements that solve a practical problem. For instance, embodiments of the present invention provide code executing on one or more processors that utilize various computing-centric data analysis and handling techniques, in order to provide one or more feedback signals to the subject's electronic device for assisting the subject in shaping the subject's behavior.

Figure 7:
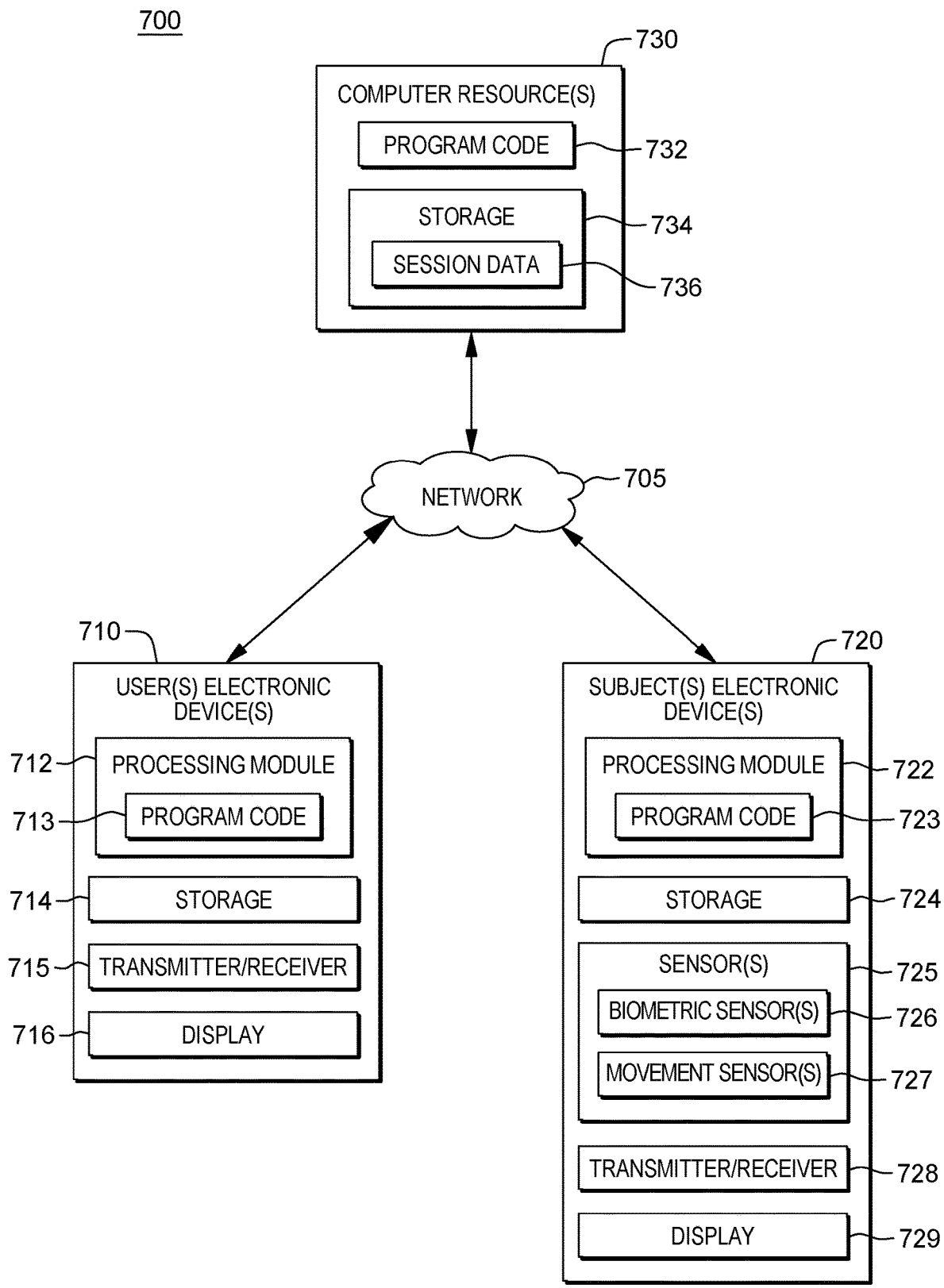
FIG. 7 depicts another embodiment of a technological environment or system in which one or more aspects of the present invention are implemented.

By way of further example, FIG. 7 depicts one embodiment of a technological environment or system 700, in which one or more illustrative embodiments described herein can be implemented. FIG. 7 is only an example, and is not intended to imply any limitation with regard to the technological environments in which aspects of the invention can be implemented. A particular implementation can have any number of modifications to the depicted environment.

As depicted in FIG. 7, system 700 includes, for instance, one or more user electronic devices 710, such as one or more mobile electronic devices associated with one or more users. In one or more embodiments, user electronic device(s) 710 can have a wireless communication capability, and can be, for instance, a smartwatch, smartglasses, a smartphone, a personal digital assistant (PDA), a wireless computer, a table, a personal communication system, etc., capable of obtaining data, performing processing and/or providing feedback signals, such as described herein.

As illustrated, user electronic device(s) 710 can include a processing module 712 with program code 714 configured to implement one or more aspects of the present invention. Further, user electronic device(s) 710 can include storage 714, for storing electronic data, as well as a transmitter/receiver 715, and a display 716, such as a touchscreen display for displaying system interfaces, such as described herein.

In one or more embodiments, program code 713 includes program instructions which implement one or more aspects of processing in accordance with the present invention. As illustrated, one or more networks 705 operatively couple user electronic device(s) 710 to one or more subject electronic device(s) 720 and/or to computer resource(s) 730. In one embodiment, subject electronic device(s) 720 can be, for instance, one or more other mobile devices, such as one or more mobile electronic devices associated with the subject. In one or more embodiments, subject electronic device(s) 720 can have a wireless communication capability, and can be, for instance, a smartwatch, smartglasses, a smartphone, a personal digital assistant (PDA), a wireless computer, a table, a personal communication system, etc., capable of obtaining data, performing processing, and/or providing feedback, such as described herein.

As illustrated, in one embodiment, subject electronic device(s) 720 can include a processing module 722 with program code 723 configured, in one or more embodiments, to facilitate performing one or more aspects of the present invention. Further, subject electronic device(s) 720 can include storage 724, as well as one or more sensors 725, such as one or more biometric sensors 726 and/or one or more movement sensors 727 (such as a gyroscope). Further, subject electronic device(s) 720 can include a transmitter/receiver 728, and a display 729. In one embodiment, the subject electronic device(s) 720 is a wearable electronic device, such as the above-noted smartwatch, smartglasses, etc. In one or more other implementations, the subject electronic device(s) is a dedicated electronic device configured to facilitate implementing one or more aspects described herein.

In one or more embodiments, network(s) 705 can be, or include, one or more wired and/or wireless networks capable of receiving and transmitting data, such as data described herein. Computer resource(s) 730 can be separate from user electronic device(s) 710 and subject electronic device(s) 720, and can be operatively coupled therewith across network(s) 705. In one specific embodiment, computer resource(s) 730 can be cloud-based computing resources. As illustrated, computer resource(s) 730 can include program code 732, which can facilitate implementing one or more aspects of processing disclosed herein in association with program code 713 executing on user electronic device(s) 710 and/or program code 723 executing on subject electronic device(s) 720. In one implementation, system processing can be distributed, with a portion of the processing being provided by user electronic device(s) 710, and another portion by computer resource(s) 730 and/or subject electronic device(s) 720. In other embodiments, various aspects of the processing described herein can be implemented principally on user electronic device(s) 710, if desired. Further, computer resource(s) 730 can include storage 734 for storing data, such as the session data 736 described herein for one or more activities of the subject.

Figure 8:
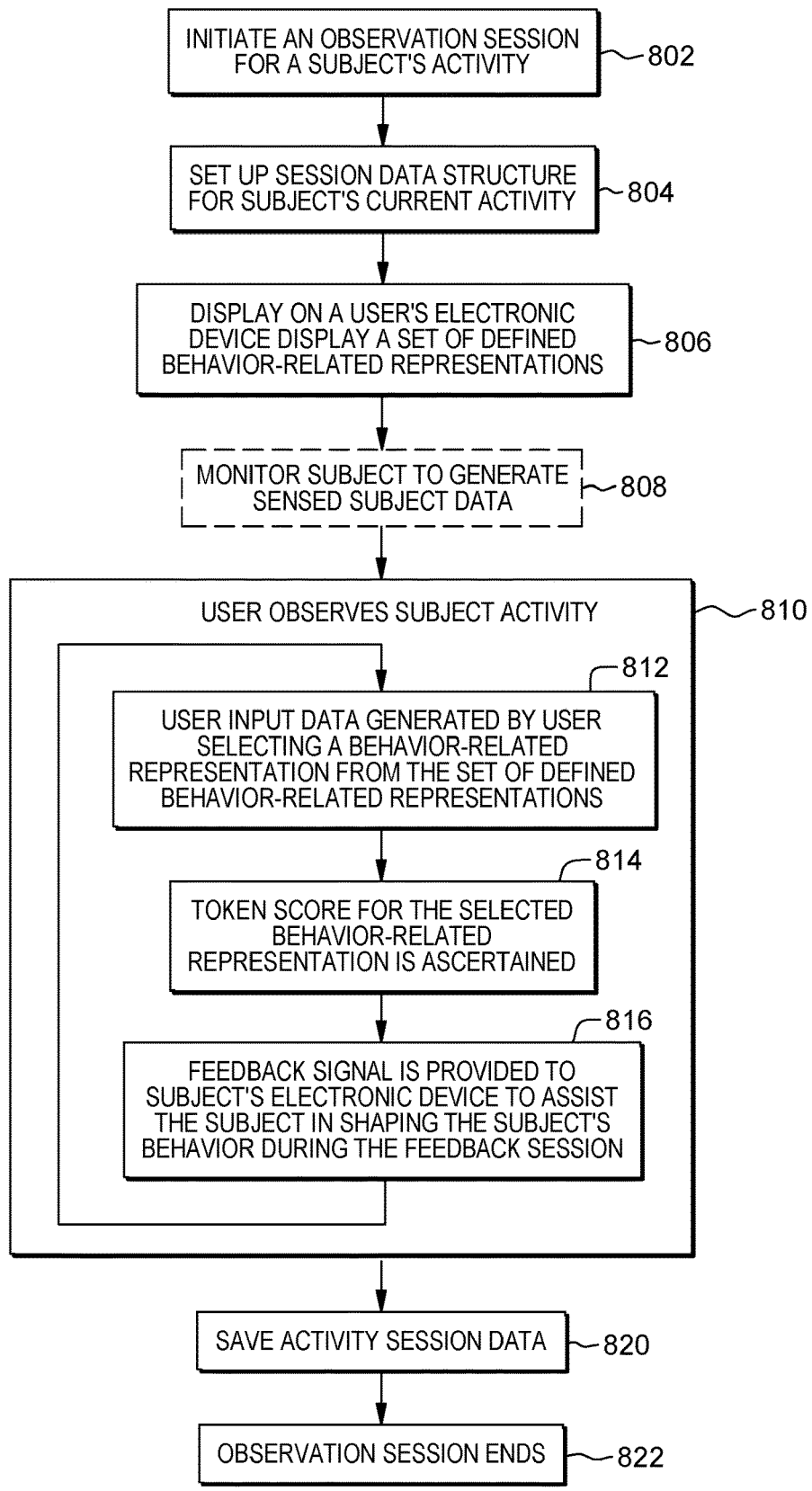
FIG. 8 is another embodiment of a process, in accordance with one or more aspects of the present invention.

By way of further example, FIG. 8 depicts another embodiment of system processing (or program code-implemented processing) of a system, a computer-implemented method, and/or computer program product, in accordance with one or more aspects disclosed herein. In one embodiment, processing 800 includes initiating an observation session for a subject's activity 802. In one example, the observation session is initiated by the user through a display interface of the user's electronic device. Based on initiation of the observation session, one or more processors set up a session data structure for the subject's current activity 804. In one embodiment, the session data structure can include the set of defined behavior-related representations for the activity of the subject, and one or more associated token scores or points associated therewith.

The set of defined behavior-related representations are displayed on the user's electronic device display 806. In one embodiment, items of the session data structure are user-selectable in response to the observed behavior of the subject during the activity.

If desired, the system can optionally monitor one or more aspects of the subject's activity, for instance, using one or more sensors or monitors. In particular, the subject can be monitored to generate sensed subject data 808, such as sensed biometric data, movement data, etc. In one embodiment, the sensed subject data can be generated by the subject's electronic device, such as the subject's wearable electronic device, or one or by more other electronic devices associated with the subject, or otherwise monitoring the subject.

As noted, during the observation session, the user observes the subject's activity 810 in order to dynamically provide real-time feedback signals to the subject, and in particular, to the subject's associated electronic device. The user can observe the subject directly, for instance, being in the same room as the subject (as illustrated in FIG. 4), or indirectly, being remote from the subject, but observing the subject via, for instance, a video monitoring of the subject (as illustrated in FIG. 5).

User input data is generated in response to the user selecting a behavior-related representation from the set of defined behavior-related representations displayed on the user's electronic device 812. Program code determines the token score for the selected behavior-related representation 814, and a feedback signal is provided to the subject's electronic device to assist the subject in shaping the subject's behavior during the feedback session 816. Upon completion of the activity, the activity session data 820 is saved (in one embodiment), and the observation session is ended 822.

Further details of one embodiment of a behavioral feedback facility, as it relates to one or more aspects of the present invention, are described with reference to FIGS. 9A-9B.

Figure 9A:
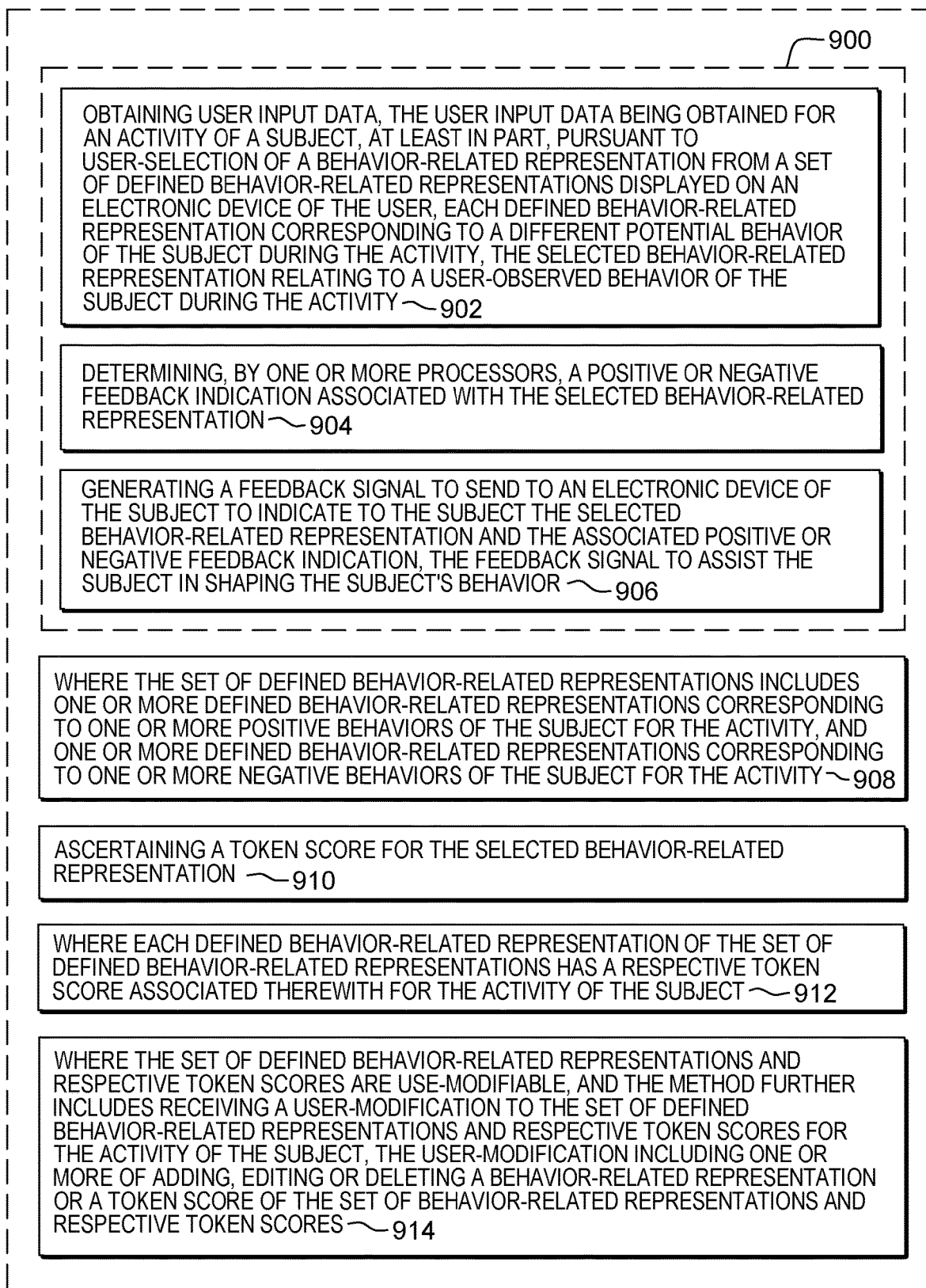

Referring to FIG. 9A, in one embodiment, a process 900 is provided which includes obtaining user input data, where the user input data is obtained for an activity of a subject, at least in part, pursuant to user-selection of a behavior-related representation from a set of defined behavior-related representations displayed on an electronic device of the user 902. Each defined behavior-related representation corresponds to a different potential behavior of the subject during the activity, and the selected behavior-related representation relates to a user-observed behavior of the subject during the activity. The method also includes determining, by one or more processors, a positive or negative feedback indication associated with the selected behavior-related representation 904, and generating a feedback signal to send to an electronic device of the subject to indicate to the subject the selected behavior-related representation and the associated positive or negative feedback indication. The feedback signal is generated to assist the subject in shaping the subject's behavior 906.

In one example, the set of defined behavior-related representations include one or more defined behavior-related representations corresponding to one or more positive behaviors of the subject for the activity, and one or more defined behavior-related representations corresponding to one or more negative behaviors of the subject for the activity 908.

In one implementation, the method further includes ascertaining a token score for the selected behavior-related representation 910. In one example, each defined behavior-related representation of the set of defined behavior-related representations has a respective token score associated therewith for the activity of the subject 912.

In one example, the set of defined behavior-related representations and respective token scores are user-modifiable, and the method further includes receiving a user-modification to the set of defined behavior-related representations and respective token scores for the activity of the subject 914. The user-modification includes one or more of adding, editing or deleting a behavior-related representation or a token score of the set of behavior-related representations and respective token scores.

Referring to FIG. 9B, in one example, the method further includes receiving a user-indication of initiation of an observation session for the activity of the subject, and based on receiving the indication, creating a session data structure identifying one or more behavior-related representations of the set of defined behavior-related representations for the activity of the subject, and logging the selected behavior-related representation and the token score in the session data structure for the observation session 916.

In one example, the method includes repeating the method for a plurality of observation sessions, and saving the session data structures for the plurality of observation sessions in a database for tracking user-observed behavior of the subject across the plurality of observation sessions for one or more activities of the subject 918.

In one embodiment, the method includes predefining the set of defined behavior-related representations for the subject and the activity from a larger group of defined behavior-related representations selectable for inclusion in the set of defined behavior-related representations, and associating a respective token score with each defined behavior-related representation in the set of defined behavior-related representations 920.

In one example, the activity is one defined activity of a plurality of defined activities for the subject, and the method further includes obtaining a respective set of defined behavior-related representations for each defined activity of the subject of the plurality of defined activities, where at least two respective sets of defined behavior-related representations obtained for at least two different defined activities include one or more different defined behavior-related representations for the different defined activities of the subject 922.

In one embodiment, the electronic device of the subject is a wearable electronic device associated with the subject, and the method further includes receiving a user-indication of initiation of an observation session for the activity of the subject, receiving biometric data of the subject during the activity, the biometric data being obtained via the wearable electronic device monitoring the subject during the activity, and saving the selected behavior-related representation and the biometric data in a session data structure for the observation session 924.

Those skilled in the art will note that a behavioral feedback system, method and computer program product are described herein for helping a user or caretaker in shaping behaviors of a subject, collect data on activities of the subject, track the data, and share the data, in a convenient, non-intrusive manner, using a mobile application on the user's electronic device, and an electronic device associated with the subject. In one or more implementations, data can be saved to a cloud-based database for sharing the data between different entities. In one example, a user defines in the mobile application a set of behaviors, both positive to encourage, and negative to discourage. The behaviors are assigned names and icons or images, representing the behavior, and the user can add, edit or delete the behaviors in the application. The user defines a list of activities or scenarios representing the environments, scenarios or circumstances under which the behavioral feedback system can be utilized, such as at school, cooking, shopping, driving, sports, etc., and assigns a list of behaviors from a master list of behaviors which they previously defined and assigned points to for the activities. In one embodiment, the subject wears the associated electronic device, such as a smartwatch, and the user utilizes the user electronic device. The user initiates execution of the particular activity or scenario previously defined, which shows the user the list or set of behaviors for that activity, along with token scores or points associated with the behaviors. In one implementation, the subject's wearable electronic device can vibrate, or provide other indicia, indicating to the subject that they either gained or lost points, with the vibration signal being different for whether points are gained or lost.

Figure 10:
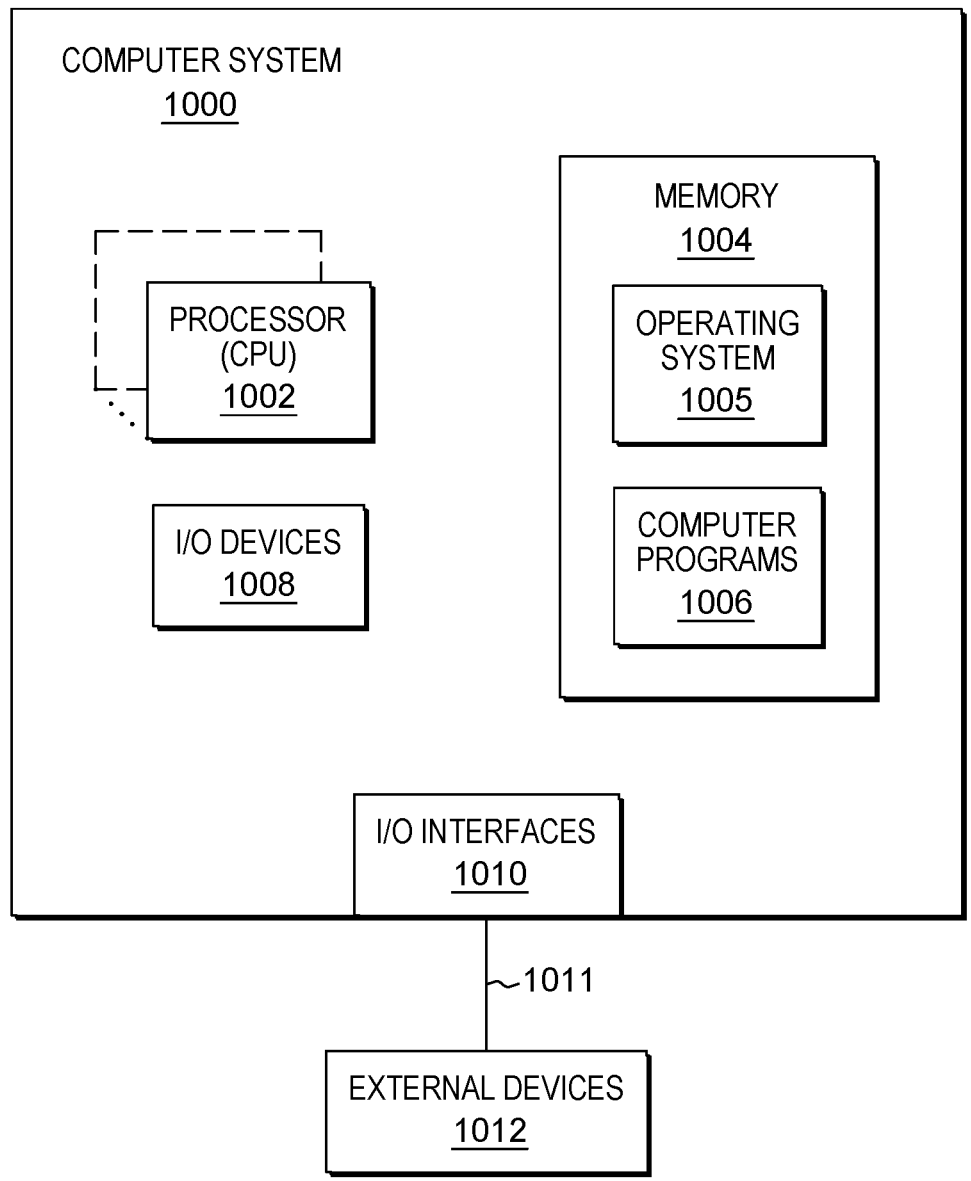
FIG. 10 depicts one embodiment of a computer system and associated devices to incorporate and/or use one or more aspects of the present invention.

By way of further example, FIG. 10 depicts a computer system 1000 in communication with external device(s) 1012, which can be used to implement one or more aspects disclosed herein. Computer system 1000 includes one or more processor(s) 1002, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 1002 can also include one or more registers to be used by one or more of the functional components. Computer system 1000 also includes a memory 1004, input/output (I/O) devices 1008, and I/O interfaces 1010, which may be coupled to processor(s) 1002 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and Peripheral Component Interconnect (PCI).

Memory 1004 can be, or include, main or system memory (e.g. Random Access Memory) used in the execution of program instructions, a storage device(s) such as hard drive(s), flash media, or optical media as examples, and/or cache memory, as examples. Memory 1004 can include, for instance, a cache, such as a shared cache, which may be coupled to local caches (examples include L1 cache, L2 cache, etc.) of processor(s) 1002. Additionally, memory 1004 can be, or include, at least one computer program product having a set (e.g., at least one) of program modules, instructions, code or the like that is/are configured to carry out functions of embodiments described herein when executed by one or more processors.

Memory 1004 can store an operating system 1005 and other computer programs 1006, such as one or more computer programs/applications that execute to perform aspects described herein. Specifically, programs/applications can include computer readable program instructions that can be configured to carry out functions of embodiments of aspects described herein.

Examples of I/O devices 1008 include but are not limited to microphones, speakers, Global Positioning System (GPS) devices, cameras, lights, accelerometers, gyroscopes, magnetometers, sensor devices configured to sense light, proximity, heart rate, body and/or ambient temperature, blood pressure, and/or skin resistance, and activity monitors. An I/O device can be incorporated into the computer system as shown, though in some embodiments an I/O device can be regarded as an external device (1012) coupled to the computer system through one or more I/O interfaces 1010.

Computer system 1000 can communicate with one or more external devices 1012 via one or more I/O interfaces 1010. Example external devices include a keyboard, a display, one or more data sensors, one or more electronic devices and/or any other devices that (for instance) enable a user to interact with computer system 1000, provide feedback signals to a subject's electronic device (e.g., smartwatch, smartglasses, etc.), and/or any other devices that facilitating implementing any other aspect described herein. Other example external devices include any device that enables computer system 1000 to communicate with one or more other computing systems or peripheral devices. A network interface/adapter is an example I/O interface that enables computer system 1000 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems. (BLUETOOTH® is a registered trademark of Bluetooth SIG, Inc., Kirkland, Wash., U.S.A.)

Communication between I/O interfaces 1010 and external devices 1012 can occur across wired and/or wireless communications link(s) 1011, such as Ethernet-based wired or wireless connections. Example wireless connections include cellular, Wi-Fi, Bluetooth®, proximity-based, near-field, or other types of wireless connections. More generally, communications link(s) 1011 can be any appropriate wireless and/or wired communication link(s) for communicating data between systems and/or devices to facilitate one or more aspects disclosed herein.

A particular external device(s) 1012 can include one or more data storage devices, which can store one or more programs, one or more computer readable program instructions, and/or data, etc. Computer system 1000 can include and/or be coupled to and in communication with (e.g. as an external device of the computer system) removable/non-removable, volatile/non-volatile computer system storage media. For example, it can include and/or be coupled to a non-removable, non-volatile magnetic media (typically called a "hard drive"), a magnetic disk drive for reading from and writing to a removable, non-volatile magnetic disk, and/or an optical disk drive for reading from or writing to a removable, non-volatile optical disk, such as a CD-ROM, DVD-ROM or other optical media.

Computer system 1000 can be operational with numerous other general purpose or special purpose computing system environments or configurations. Computer system 1000 can take any of various forms, well-known examples of which include, but are not limited to, personal computer (PC) system(s), server computer system(s), thin client(s), thick client(s), workstation(s), laptop(s), handheld device(s), mobile device(s)/computer(s), such as smartphone(s), tablet(s), and wearable device(s), multiprocessor system(s), microprocessor-based system(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

As will be appreciated by one skilled in the art, control aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, control aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may be any non-transitory computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

In one example, a computer program product includes, for instance, one or more computer readable storage media to store computer readable program code means or logic thereon to provide and facilitate one or more aspects of the present invention.

Program code embodied on a computer readable medium may be transmitted using an appropriate medium, including but not limited to wireless, wireline, optical fiber cable, RF, etc., or any suitable combination of the foregoing.

Computer program code for carrying out control and/or calibration operations for aspects of the present invention may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to block diagrams of methods, apparatus (systems) and computer program products according to embodiments of the invention. It will be understood that the control block of the diagram can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus (e.g., mobile device/phone), or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The block diagram in the figure illustrates the architecture, functionality, and operation of possible implementations of systems, methods and computer program products according to various embodiments of the present invention. In this regard, one or more blocks in the diagram may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that one or more blocks of the diagram can be implemented by special purpose hardware-based systems that perform the specified functions or acts, or combinations of special purpose hardware and computer instructions.

In addition to the above, one or more aspects of the present invention may be provided, offered, deployed, managed, serviced, etc. by a service provider who offers management of customer environments. For instance, the service provider can create, maintain, support, etc. computer code and/or a computer infrastructure that performs one or more aspects of the present invention for one or more customers. In return, the service provider may receive payment from the customer under a subscription and/or fee agreement, as examples. Additionally or alternatively, the service provider may receive payment from the sale of advertising content to one or more third parties.

In one aspect of the present invention, an application may be deployed for performing one or more aspects of the present invention. As one example, the deploying of an application comprises providing computer infrastructure (including, e.g., internet/cloud/IOT resources and/or a mobile device) operable to perform one or more aspects of the present invention.

As a further aspect of the present invention, a computing infrastructure may be deployed comprising integrating computer readable code into a computing system, in which the code in combination with the computing system is capable of performing one or more aspects of the present invention.

As yet a further aspect of the present invention, a process for integrating computing infrastructure comprising integrating computer readable code into a computer system may be provided. The computer system comprises a computer readable medium, in which the computer medium comprises one or more aspects of the present invention. The code in combination with the computer system is capable of performing one or more aspects of the present invention.

Although various embodiments are described above, these are only examples. For example, computing environments of other architectures can incorporate and use one or more aspects of the present invention. Additionally, the network of nodes can include additional nodes, and the nodes can be the same or different from those described herein. Also, many types of communications interfaces may be used.

Further, a data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, mobile device/phone, keyboards, displays, pointing devices, DASD, tape, CDs, DVDs, thumb drives and other memory media, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to explain the principles of the invention and the practical application, and to enable others of ordinary skill in the art to understand the invention through various embodiments and the various modifications thereto which are dependent on the particular use contemplated.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An electronic communication method comprising:
configuring a user mobile device with communication session code for multiple potential subject actions, the communication session code comprising a plurality of displayable icons selectively displayable on a display of the user mobile device for the multiple potential subject actions;

preconfiguring, by the user, the communication session code for a particular subject activity to display on the user mobile device a preconfigured icon subset of displayable icons of the plurality of displayable icons for the particular subject activity, the preconfigured icon subset facilitating communicating silently in real time with a subject wearable device during the particular subject activity, and the preconfigured icon subset including displayable icons for multiple positive subject actions for the particular subject activity and displayable icons for multiple negative subject actions for the particular subject activity, wherein the displayable icons of the multiple positive subject actions each have a respective positive token score associated therewith for the particular activity of the subject, and the displayable icons of the multiple negative subject actions each have a respective negative token score associated therewith for the particular activity of the subject;

electronically communicating in real time silently with the subject via the user mobile device and the subject wearable device, the subject wearable device being worn by the subject, the electronically communicating in real time comprising:

executing the communication session code on the user mobile device, and initiating an electronic communication session for the particular subject activity between the user mobile device and the subject wearable device, the executing including displaying on the user mobile device display the icon subset preconfigured by the user for the particular subject activity; and during the electronic communication session, wirelessly transmitting by the user mobile device an electronic feedback signal to the subject wearable device, the electronic feedback signal comprising a vibrate signal to vibrate in real time the subject wearable device and an image icon for display in real time on a display of the subject wearable device, the electronic feedback signal being related to and transmitted in real time based on a selection of a particular icon of the preconfigured icon subset displayed on the display of the user mobile device for the particular subject activity, wherein the electronic feedback signal further includes a positive or negative feedback signal based on the respective positive token score or respective negative token score of the selected particular icon of the preconfigured icon subset displayed on the display of the user mobile device for the particular subject activity.

2. The electronic communication method of claim 1, wherein the display of the usable device comprises a touch screen display, and wherein the wirelessly transmitting by the user of the electronic feedback signal to the subject wearable device is based on selection via the touch screen of the particular icon of the preconfigured icon subset displayed on the display of the user mobile device of the particular subject activity.

3. The electronic communication method of claim 1, wherein executing the communication session code on the user mobile device further comprises generating a communication session data structure containing data representative of the electronic communication session.

4. The electronic communication method of claim 3, further comprising repeating the initiating the electronic communication session and the wirelessly transmitting for a plurality of electronic communication sessions for the particular subject activity, and saving generated session data structures for the plurality of electronic communication sessions in a database.

5. The electronic communication method of claim 1, further comprising preconfiguring, by the user, the communication session code for multiple different subject activities to display on the user mobile device a respective, preconfigured icon subset of displayable icons of a plurality of displayable icons for each subject activity of the multiple different subject activities, where at least two preconfigured icon subsets of displayable icons for at least two respective subject activities include one or more different displayable icons of the plurality of displayable icons.

6. The electronic communication method of claim 1, further comprising generating, by the subject wearable device, biometric data of the subject during the particular subject activity, and saving the generated biometric data in a session data structure for the electronic communication session along with data representative of the wireless transmitting of the electronic feedback signal to the subject wearable device.

7. A system for electronically communicating in real time with a subject, the system comprising:

a user mobile device configured with communication session code for multiple potential subject actions, the communication session code comprising a plurality of displayable icons selectively displayable on a display of the user mobile device for the multiple potential subject actions, and the communication session code being preconfigured, by a user, for a particular subject activity to display on the user mobile device a preconfigured icon subset of displayable icons of the plurality of displayable icons, the preconfigured icon subset facilitating communication in real time with the subject during the particular subject activity, and the preconfigured icon subset including displayable icons for multiple positive subject actions for the particular subject activity and displayable icons for multiple negative subject actions for the particular subject activity, wherein the displayable icons of the multiple positive subject actions each have a respective positive token score associated therewith for the particular activity of the subject, and the displayable icons of the multiple negative subject actions each have a respective negative token score associated therewith for the particular activity of the subject;

a subject wearable device, the subject wearable device being a wearable electronic device worn by the subject;

wherein the system is configured to execute communication session code on the user mobile device to initiate an electronic communication session for the particular subject activity between the user mobile device and the subject wearable device, where executing the communication session code includes displaying on the user mobile device display the icon subset preconfigured by the user for the particular subject activity; and wherein the user mobile device wirelessly transmits, during the electronic communication session, an electronic feedback signal to the subject wearable device, the electronic feedback signal comprising a vibrate signal to vibrate in real time the subject wearable device and an image icon for display in real time on a display of the subject wearable device, the electronic feedback signal being related to and transmitted in real time based on a selection of a particular icon of the preconfigured icon subset displayed on the display of the user mobile device for the particular subject activity, wherein the electronic feedback signal further includes a positive or negative feedback signal based on the respective positive token score or respective negative token score of the selected particular icon of the preconfigured icon subset displayed on the display of the user mobile device for the particular subject activity.

8. The system of claim 7, wherein the display of the user mobile device comprises a touch screen display, and wherein the electronic feedback signal is wirelessly transmitted to the subject wearable device based on selection via the touch screen of the particular icon of the preconfigured icon subset displayed on the display of the user mobile device for the particular subject activity.

9. The system of claim 7, wherein the communication session code is configured to generate a communication session data structure containing data representative of the electronic communication session when run on the user mobile device.

10. The system of claim 9, wherein the communication session code is configured to save generated session data structures for a plurality of electronic communication sessions in a database with running of the communication session code on the user mobile device for the particular subject activity.

11. The system of claim 7, wherein the communication session code is preconfigured by the user for multiple different subject activities to display on the user mobile device a respective, preconfigured icon subset of displayable icons of the plurality of displayable icons for each subject activity of the multiple different subject activities, where at least two preconfigured icon subsets of displayable icons for at least two respective subject activities include one or more different displayable icons of the plurality of displayable icons.

12. The system of claim 7, further comprising a biometric sensor associated with the subject wearable device to generate biometric data of the subject during the particular subject activity, the generated biometric data being received at the user mobile device, and the communication session code being configured to save generated biometric data in a session data structure for the electronic communication session along with data representative of the electronic feedback signal wirelessly transmitted to the subject wearable device.

13. An electronic communication method comprising:
configuring a user mobile device with communication session code for multiple potential subject actions, the communication session code comprising a plurality of displayable icons selectively displayable on a display of the user mobile device for the multiple potential subject actions;
preconfiguring, by the user, the communication session code for a particular subject activity to display on the user mobile device a preconfigured icon subset of displayable icons of the plurality of displayable icons for the particular subject activity, the preconfigured icon subset facilitating communicating silently in real time with a subject wearable device during the particular subject activity, and the preconfigured icon subset including displayable icons for multiple positive subject actions for the particular subject activity and displayable icons for multiple negative subject actions for the particular subject activity, wherein the displayable icons of the multiple positive subject actions each have a respective positive token score associated therewith for the particular activity of the subject, and the displayable icons of the multiple negative subject actions each have a respective negative token score associated therewith for the particular activity of the subject;
dynamically modifying, by the user, at least one positive token score or negative token score of at least one icon of the preconfigured icon subset of displayable icons for an electronic communication session for the particular subject activity;
electronically communicating in real time silently with the subject via the user mobile device and the subject wearable device, the subject wearable device being worn by the subject, the electronically communicating in real time comprising:
executing the communication session code on the user mobile device, and initiating the electronic communication session for the particular subject activity between the user mobile device and the subject wearable device, the executing including displaying on the user mobile device display the icon subset preconfigured by the user for the particular subject activity; and
during the electronic communication session, wirelessly transmitting by the user mobile device an electronic feedback signal to the subject wearable device, the electronic feedback signal comprising a vibrate signal to vibrate in real time the subject wearable device and an image icon for display in real time on a display of the subject wearable device, the electronic feedback signal being related to and transmitted in real time based on a selection of a particular icon of the preconfigured icon subset displayed on the display of the user mobile device for the particular subject activity, wherein the electronic feedback signal further includes a positive or negative feedback signal based on the respective positive token score or respective negative token score of the selected particular icon of the preconfigured icon subset displayed on the display of the user mobile device for the particular subject activity.

\* \* \* \* \*